United States Patent [19]

Furlan et al.

[11] Patent Number: 5,785,983
[45] Date of Patent: Jul. 28, 1998

[54] NON-POROUS COLLAGEN SHEET FOR THERAPEUTIC USE, AND THE METHOD AND APPARATUS FOR PREPARING IT

[75] Inventors: Diego Furlan, Segrate; Giovanni Bonfanti, Formia Santa Croce; Giuseppe Scappaticci, Cassino, all of Italy

[73] Assignee: Eurorestearch Srl, Milan, Italy

[21] Appl. No.: 155,785

[22] Filed: Nov. 23, 1993

Related U.S. Application Data

[63] Continuation-in-part of Ser. No. 883,362, May 15, 1992, abandoned.

[30] Foreign Application Priority Data

May 23, 1991 [IT] Italy ................... MI91A1423

[51] Int. Cl.$^6$ ........................... A61K 38/01
[52] U.S. Cl. ............... 424/423; 424/443; 424/444; 424/445; 514/801; 530/356
[58] Field of Search ............... 514/801; 602/50; 530/356; 424/443, 445, 423, 444

[56] References Cited

U.S. PATENT DOCUMENTS

| | | | |
|---|---|---|---|
| 3,152,203 | 10/1964 | Dumitru | 530/356 |
| 3,293,237 | 12/1966 | Wiegand | 530/356 |
| 3,529,530 | 9/1970 | Tsuzuki | 264/202 |
| 4,970,298 | 11/1990 | Silver et al. | 530/356 |
| 4,997,659 | 3/1991 | Yatka et al. | 426/548 |
| 5,028,329 | 7/1991 | Drioli et al. | 210/490 |
| 5,086,078 | 2/1992 | Harclerode et al. | 521/58 |
| 5,202,120 | 4/1993 | Silver et al. | 424/93 |
| 5,219,895 | 6/1993 | Kelman et al. | 522/68 |

OTHER PUBLICATIONS

Gorham et al., Biomats., 11, pp. 113–118, 1990.

Sigma Chemical Company, 1991 Catalog of Biochemicals, Organic Compounds for Research and Diagnostic Reagents (Collagen); (Dec. 1990).

Eurorsearch s.r.l., GELFIX, Collagen Catalog (year unavailable).

Diamond et al., "The Effect of Modification on the Susceptibility of Collagen to Proteolysis:I. Chemical Modification of Amino Acid Side Chains", MATRIX, vol. 11/1991 pp. 321–329 (Nov. 1991).

111 Colorimetric Methods of Analysis, D. Van Nostrand Co. 1954, pp. 195–196.

*Primary Examiner*—Jeffrey Mullis
*Attorney, Agent, or Firm*—Stevens, Davis, Miller & Mosher, L.L.P.

[57] ABSTRACT

Type I collagen gel with an $H_2O$ content not exceeding 20% by weight, in the form of a sheet of thickness between 0.02 and 2 mm, of compact transparent structure, with a capacity for absorbing aqueous biological liquids limited to a maximum of 15 times its weight, being free from native collagen degradation products, and suitable for the therapeutic treatment of wounds and burns.

14 Claims, 1 Drawing Sheet

NON-POROUS COLLAGEN SHEET FOR THERAPEUTIC USE, AND THE METHOD AND APPARATUS FOR PREPARING IT

This application is a continuation-in-part of application Ser. No. 07/883,362, filed May 15, 1992, now abandoned.

Collagen is a scleroprotein widespread in nature. It represents about one third of the total proteins of the human body. Medical practice has recently seen the introduction of the use of collagen as a stimulating agent in the cicatrization process involving an interaction effect with various growth factors, because of its capturing action on fibronectin, a glycoprotein which promotes cell attachment and the migration and replication of the resultant cells (see "Il collageno nella cicatrizzazione" by B. Palmieri, publ. Artestampa, Jan. 1990, pp. 40–42) and other actions which are still not totally clear. The known collagen product, using a particular non-denaturing process, is prepared in stable form by a process of extraction from animal organs rich in this scleroprotein, purification and subsequent lyophilization. The final product is in the form of mats of greater or lesser thickness, characterised by high absorbent power (exudates and liquids in general) because of its structure in the form of fibres which are spaced apart and branched in such a manner as to make a large specific surface available for absorption (up to 50 times its weight). The hydrophilic nature of collagen also greatly favours this absorbent power.

In addition to the aforesaid function, the role of collagen in cicatrization is characterised by collagen/platelet interaction and the formation of a bond between the collagen, the fibronectin and the growth factors, molecules which are known to be implicated in regulating the cicatrization process (see pages 45–46 of the aforesaid text).

There are however cases in which the absorbent formation of the collagen sponge and its hydrophilic nature lead to an excessive loss of physiological liquids. It is well known that an evaporation process normally occurs through the undamaged skin, and this increases considerably in the case of skin lesion, resulting in dehydration of the underlying layers. The phenomenon is accentuated for example in burn cases, when large skin portions are damaged traumatically. In this case the absorbent effect of lyophilized collagen further increases the process of evaporation, with consequent damage to the underlying structure.

In addition to lyophilized collagen sponge, other collagen based products are known from the prior art and find application in medical practice as well as in biological research.

Collagen based compositions for medical use are disclosed by USP 4,970,298, which claims three dimensional matrices of carbodiimide and dehydrotermal cross-linked collagen fibers useful for treating skin wounds, and by USP 5,219,895, which claims a collagen product suitable for bonding soft tissues, and particularly for sealing incisions following cataract removal, said collagen product being obtained by reacting a partially fibrillar collagen with an acylating agent or a sulfonating agent. Both USP 4,970,298 and in USP 5,219,895 relates to chemically modified collagens.

Dumitri E.T. (USP 3,152,203) discloses collagen sheets supported onto resinous films, useful as substrates in cell culture. The kind of collagen used in USP 3,152,203 is a water soluble collagen, which is therefore different from type I collagen, which is insoluble in various types of aqueous media, such as biological liquids.

The present invention provides a sheet of chemically unmodified type I collagen, obtained by a process comprising a filtering step and a drying step, which while maintaining the rapid cicatrization characteristics of collagen, at the same time prevents excessive evaporation, allows constant inspection of the bed of the wound without having to be removed (transparency), is simple and practical to use, adheres satisfactorily to the injured surface, does not require frequent replacement, can transpire to allow oxygenation of the bed of the wound while preventing its contamination by bacteria, is absorbable but not soluble in the biological liquids with which it comes into contact, unless by specific enzymatic action, and is structurally homogeneous.

Another important characteristic of the collagen according to the invention is that of being suitable as interposition material for preventing adhesions in the internal surgery operations.

To obtain a product with these characteristics, type I collagen was used as defined in Table 1 herein below reported, this having the characteristic of being insoluble in the various types of biological liquids. The type I collagen used as starting material in the present invention can be prepared according to the method of Einbinder J., and Schubert M. (J. Biol. Chem., 188, 335, 1951) or can be purchased from SIGMA [R] (see the Sigma Catalog "Biochemicals Organic Compounds for Reasearch and Diagnostic Reagents", 1991, pag. 276).

TABLE 1

Collagen: some types, molecular structure and tissue distribution

Type I - Molecular structure: [α1(I)$_2$α2(I)]
Tissue distribution

Normal regular and flail connective tissue, fibrocartilage, bone, dentin. It derives from fibroblasts, reticular cells, smooth muscular cells, osteoblasts and odontoblasts.
Practically ubiquitariam.
Trimer type I variant, [a1(I)]$_3$, was found in embryonal tissues, phlogistic areas and tumors.

Type II - Molecular structure: [α1(II)]$_3$
Tissue distribution

It is specifically found in cartilage (hyaline and elastic), in some eye and vitreous body structures. It is produced by chondrocytes and retinal cells.

Type III - Molecular structure: [α1(III)]$_3$
Tissue distribution

It is present in flail connective tissue and reticular fibers, dermis and vessels. It is produced by fibroblasts and reticular cells, by smooth muscular and endothelial cells and it may be found where the type I collagen is, but in particular in elastic tissues (lung, intestinum, liver and vessels) and in proliferative tissues (fetals).

Type IV - Molecular structure: [α1(IV)]$_2$α2(IV)
Tissue distribution

It is the typical collagen of the basal membrane. It reachs high concentrations in the anterior region of crystalline, glomerule and placenta. It is produced by epithelial and endothelial cells.

Type V - Molecular structure:
[α1(V)]$_2$α2(V) α1(V), α2(V), α3(V) o [α3(V)]$_3$
Tissue distribution It is a collagen present at the cell surface. It is particularly found in (smooth) muscular tissue as the chorionic amniotic membranes and in capilliary vascular structure. In lower amount in bone and in cartilage.

Type VI - Molecular structure: [α1(VI)]$_3$
Tissue distribution

Initially isolated from pepsinic digestion of the aortic (intima) paries; it is practically ubiquitariam and it may be found in very low amount (<1%) in tissues containing type I collagen.

Type VII
Tissue distribution

It is isolated from amniotic membranes and it would have an important structural role in the basal membranes.

Type I collagen present in the skin represents about 80% of the total located in the deep dermis, 90–95% in the tendons and 100% in the bones. Type I collagen is therefore the most biologically similar to that present in the human skin.

Because of its insolubility, in order to obtain a product of homogeneous structure, use was made of the known method of dispersing fibrous collagen in a dilute acetic acid solution of about pH 2.5 and maintaining agitation until a good dispersion of the collagen fibres in the liquid is obtained. At this pH value the fibres swell to form a gel. The dispersion can be effected at temperatures ranging from 0° and +30° C. and, depending on the apparatus used, different gelation speeds may be used. Typically, at the begininning of the gelation a stirring speed of about 50 r.p.m. is used, which is gradually decreased up to 5 r.p.m., so to avoid excessive air absorption. The gel obtained, still comprising fibre fractions which have not completely gelled and possibly corpuscles of extraneous substances, is further diluted with an acetic acid solution of pH 2.5–3.5 until a sufficiently fluid mass is obtained, which is then filtered.

The filtering, which is done under vacuum, uses a special filter, indicative (but not limitative) characteristics of which are given hereinafter, and allows practically total elimination of the inevitable air bubbles which form during gelling and are difficult to eliminate given the viscosity of collagen gel.

By the effect of the vacuum, which has to be of the order of 30 mm Hg residual pressure, these bubbles increase their volume, the passage through the mesh then breaks down and eliminates them. It has been found experimentally that the best filtration conditions to achieve the described phenomenon are a gel temperature of 10°–30° C., preferably 25°–28° C., and a residual vacuum of 20–60 mm Hg, preferably about 30 mm Hg.

These data are indicative and have been found experimentally to be the most effective, although not representing a limitation on the operating conditions of this process.

The filtered gel is collected in a closed vessel maintained under vacuum and constructed in such a manner that the filtered gel runs along vessel partition walls located below the filter mesh and structured to produce a continuous liquid film which does not allow further air absorption after filtration, following inclusion of air bubbles.

The filtered gel is further maintained under vacuum at 20–25 mm Hg for a further hour to allow total elimination of any air bubbles which may still be present in the gel.

FILTER APPARATUS

The filter required for filtering the collagen gel, which besides eliminating the solid particles, which are retained on the mesh, also eliminates the air bubbles contained in it, consists of an upper cylindrical stainless steel shell provided with a scraping stirrer to keep the collagen gel mixed and to remove solid particles from the mesh so that they do not clog it. The bottom of the cylindrical shell houses a stainless steel mesh with a mesh size of less than 0.1 mm (Taurail meshes have been found to be particularly effective).

The lower part (below the mesh) consists of a cylindrical shell in which vacuum can be generated by a suitable pump. The air bubbles contained in the gel which filters through the mesh increase considerably in volume because of the vacuum.

At about 3 mm below the filter mesh there is a device consisting of a series of stainless steel plates which are vertically or raking placed and parallel between them. Alternatively, the plates can be radially arranged around the cylindrical shell axis. The plates of the device are less long than the lower cylindrical shell, and are as long as it is practical to convey the filtered gel towards the bottom of the lower shell while providing in the bottom portion of the lower shell a zone having suitable lenghth to collect the filtered gel. The filtered gel descends along these plates in the form of a continuous liquid film and runs by gravity towards the bottom of the vessel.

Figure 2:
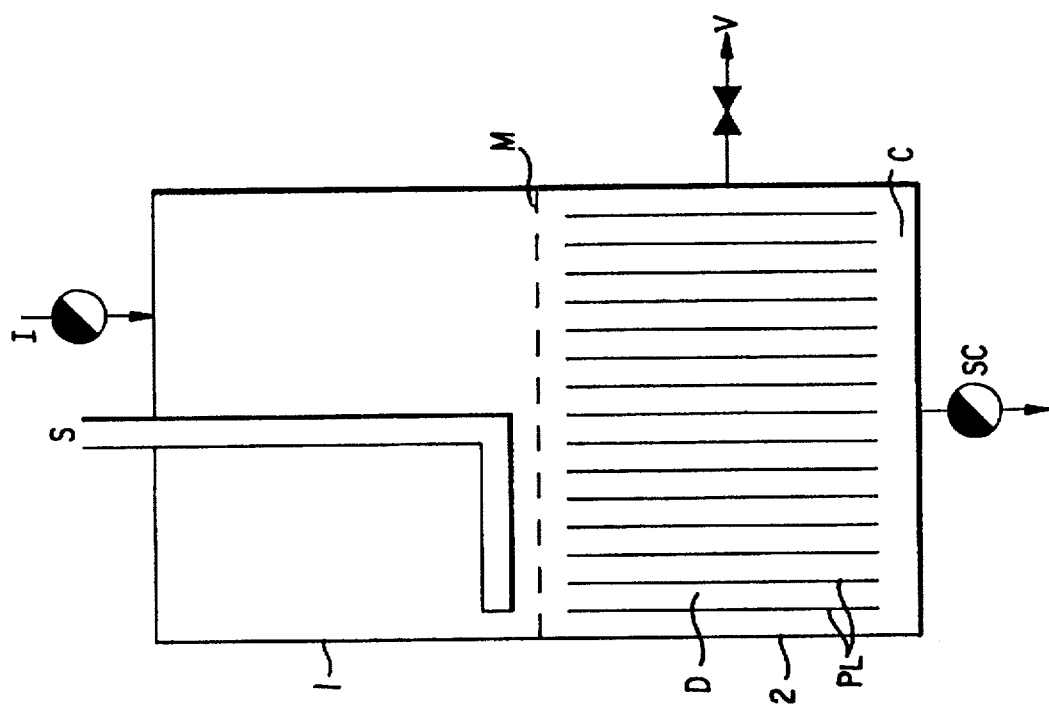
FIG. 2 shows a cross-sectional view of a filter in accordance with the present invention.

An embodiment of a filter according to the present invention is illustrated in FIG. 2. In this, the reference numeral 1 indicates the upper cylindrical shell, I indicates an inlet suitable for feeding the collagen gel to be filetered, S indicates the scraping stirrer, M indicates the mesh, V indicates the valve connected with the vacuum pump, the reference numeral 2 indicates the lower cylindrical shell, D is the device conveying a continuous film of filtered gel towards the bottom of the shell 2, PL are the plates forming said device, C is the bottom part of the lower shell wherein the filtered gel is collected, SC is an outlet suitable for discharging the filtered gel.

Those air bubbles which do not break down by the effect of the reduced pressure remain mainly in the upper part of the device whereas the gel, now free or almost free of air, runs to the bottom of the vessel. Any very small bubbles still present in the filtered gel decrease considerably in volume when returned to atmospheric pressure, so that they become practically absent.

In this respect, during filtration because of the difference between the pressure of the gel environment before filtration and the residual pressure below the mesh (about 30 mm Hg), the bubble volume increases more than 25 times. Likewise, on passing from vacuum to the environmental pressure the bubble volume decreases 25 times. Hence the air bubbles of diameter less than 0.100 mm (advisable mesh passage size) have a diameter of less than 0.034 mm when returned to atmospheric pressure, ie are practically invisible. During drying, these residual bubbles are eliminated without leaving appreciable craters in the structure of the obtained sheet.

This means that extremely uniform thicknesses can be obtained over the entire sheet surface, so avoiding any porosity which could represent a point of preferential attack by enzymatic action, which would annul the protective effect against invasion by micro-organisms.

DRYING

The filtered gel obtained as described, free from extraneous particles and air bubbles and perfectly clear and transparent, can then be used for preparing films of desired thickness and diameter. For this, after analysis to exactly determine the concentration of the filtered gel, exactly measured quantities for obtaining films with the desired collagen thickness must be metered into suitable containers. Typically, a filtered gel having a collagen concentration between about 0.1% and 0.5% (weight/weight) is used, the preferred concentration being 0.5%. At lower concentration values, too long drying times are required, thus increasing the costs, while when the collagen concentration is greater than 0.5% the product is not fluid enough to be loaded onto the drying trays in the form of uniform layers. This metering is generally effected by a suitable peristaltic pump which prevents incorporating air into the gel while at the same time preventing heating or friction which could damage the structure of the collagen protein. The containers are of tray shape and are formed of antiadherent material (for instance teflon). The amount of filtered gel to be loaded onto the trays varies from 0.4 to 4 g/cm², and preferably from 0.4 to 2 g/cm². In this way, gel levels between 4 to 40 mm are obtained. The described trays loaded with the gel in a controlled environment (relative humidity 60–80%, temperature 20°–22° C., environment class 10.000 or less) are placed in a suitable controlled drying oven where they are left to stand for at least two hours to obtain perfect gel thickness uniformity. In the present application, the definition of the environmental class is made in accordance with internationally recognized criteria. More precisely, an environment class 10.000 refers to an environment with less than 10.000 motes in a cubic foot. The motes are removed from air by means of suitable filters and the detection of the residual motes is made with an electronic apparatus able to count particles of size greater than 0.05 microns.

The oven is purged with a nitrogen stream for about 30 minutes to totally eliminate air and remove oxygen, in order to ensure constant operating conditions and prevent possible oxidation.

This operation has also been shown to practically totally block the growth of micro-organism colonies, which sometimes occurs if the procedure is carried out with air present in the environment. Drying is effected in a nitrogen stream under closed cycle.

Figure 1:
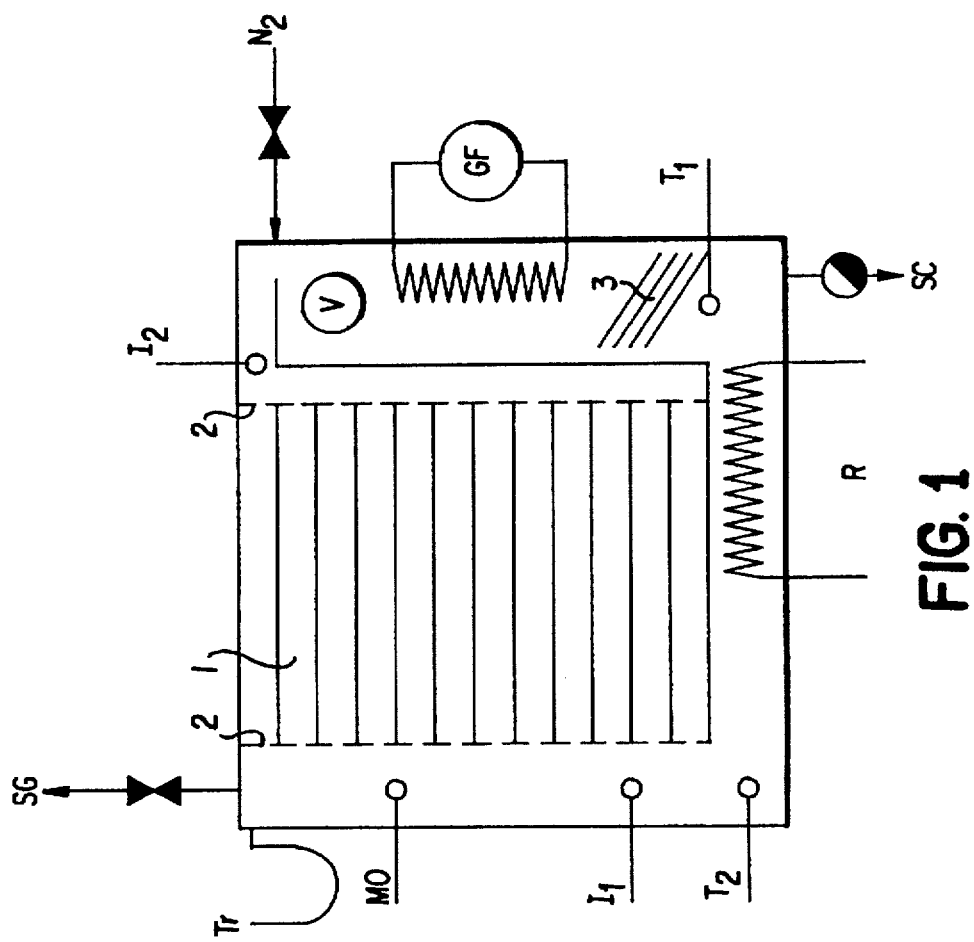
FIG. 1 shows a cross-sectional view of a drying oven suitable for obtaining the sheet of collagen gel in accordance with the present invention.

The drying, being the critical stage for obtaining films with the desired characteristics, is conducted under particular conditions in an appropriate oven shown schematically in FIG. 1.

In this, the reference numeral 1 indicates the drying trays resting on perforated side walls 2. V indicates the fan for circulating nitrogen through the apparatus, $N_2$ indicates the nitrogen feed valve, GF indicates the refrigeration unit with coil, S represents a parallel plate device for separating condensate droplets, $T_1$ indicates a first thermometer, SC indicates the condensed water discharge, R indicates the heating device, $T_2$ indicates a second thermometer, $I_1$ indicates a first hygrometer, MO indicates an oxygen meter (analyzer), Sg indicates the gas discharge, Tr indicates an overpressure trap and $I_2$ indicates a second hygrometer.

The oven is arranged in this manner to satisfy the following requirements:

1) the facility for eliminating air by purging with nitrogen to a residual oxygen content of less than 2%;

2) the facility for varying the nitrogen cooling and heating temperature to a maximum of 30° C., to control the relative humidity in the drying chamber and the water evaporation rate;

3) the facility for regulating the rate of nitrogen circulation through the chamber so as not to create high flow points and hence maintain a uniform drying rate over the entire surface and prevent the formation of creases which, besides being undesirable from the appearance aspect, are an indication of different collagen concentrations and poor homogeneity of drying (localized drying). The $H_2O$ content of the product must not be higher than 20% by weight. It is preferable to achieve a higher level of drying (down to 2% or 3% of $H_2O$), in particular to ensure proper elimination of the acetic acid present in the initial gel. The dried product obtained easily reabsorbs moisture from the environment, while being maintained within the maximum limit of 20%.

Typically, the water is removed by blowing onto the sheets of collagen gel to be dried a nitrogen stream (with an oxygen content lower than 2%) having a suitable relative humidity degree, adjusted by trial depending on the water content of the material to be processed. The relative humidity of the nitrogen stream which is blown onto the sheets of collagen gel can be comprised in a wide range, such as between 1% to 95%, and is controlled by varying the nitrogen temperature.

Particularly, the water is gradually removed by gradually decreasing the relative humidity of the nitrogen stream blown onto the collagen sheet during subsequent drying stages, the number of a greater number of stages being required for the products having a greater water content.

For instance, a nitrogen stream having a relative humidity between 1% to 30%, at a temperature between +20° and +30° C., and preferably of +26°/+28° C., is blown onto the sheets of collagen to be dried, and after the contact with said sheets, the nitrogen stream, which generally has a relative humidity between 30% to 95%, is cooled to a suitable temperature so to reduce the relative humidity to the desidered value by condensing the water. To this aim, nitrogen is generally cooled to temperatures between –40° to 0° C.

Other than nitrogen, other inert gases chemically compatible with collagen could be used, even though nitrogen is the more convenient from an economic point of view.

It is important to underline that the present overall process for preparing the sheet of collagen of the invention is a mild procedure which allows the native structure of type I collagen used as starting material to be maintained.

EXAMPLE

PREPARATION OF A SHEET OF TYPE I COLLAGEN ACCORDING TO THE INVENTION a) Gel preparation Commercially available type I collagen (purchased from SIGMA$^R$) is dispersed according to conventional techniques in a dilute aqueous acetic acid solution of pH 2.5, at a temperature of 18°–20° C.

The stirring speed during the gel preparation depends on the gelation apparatus. Typically, at the beginning of the gelation a stirring speed of about 50 r.p.m. is used, which is gradually decreased up to 5 r.p.m. so to avoid excessive air absorption.

b) Gel filtration

The collagen gel so obtained is analysed so to exactly determine the collagen content, then it is further diluted with a 0.5% weight/volume acetic acid aqueous solution up to a final collagen concentration of 0.5% (weight/weight).

The diluted gel prepared as described above is filtered in a filter in accordance with the present invention, under vacuum (20–60 mm Hg), at a temperature of +25°/+28° C., at a filtering speed of 200 liters per hour.

Particularly, a filter comprising two stainless steel cylindrical shells having a 60 cm. diameter was used. The upper shell is provided with an inlet suitable to feed the collagen gel and with a scraping stirrer. The bottom of the upper shell houses a stainless steel mesh with a mesh size of less than 0.1 mm. The lower cylindrical shell is an hermetic seal vessel, connected by a suitable valve with a vacuum pump and provided with a second valve to feed air at the end of the filtration. The lower cylindrical shell is provided with a device which conveys the filtrate through the mesh towards the bottom of the lower shell in the form of a continuous liquid film.

The device, which is placed at 3 mm below the mesh, consists of a series of stainless steel plates, vertically placed with respect to the shell bottom and are arranged in parallel between them.

c) Gel drying

The filtered gel obtained as described has a collagen concentration of 0.5% (weight/weight).

Trays of antiadherent material (for instance teflon) are loaded with an amount of filtered gel of 10 mm by means of a peristaltic pump, in a controlled environment (relative humidity=60–80%; temperature 20°–22° C.; environment class at least 10,000).

The trays loaded with the filtered gel are placed in a drying oven according to the invention, with an oxygen content of less than 1% (obtained according to 1st stage as described below) and left to stand 1 hour.

The drying process is then effected under the conditions described for stages 2–5.

The conditions found experimentally to be most appropriate for conducting a drying cycle are given below by way of non-limiting example.

1st stage:
Nitrogen purging until the oxygen content is less than 1%, standing for two hours to come to equilibrium, loaded gel level 10 mm, gel collagen concentration 0.5%.

2nd stage:
Starting of nitrogen circulation by fan.
Nitrogen temperature after cooling –5° C. ($T_1$).
Nitrogen temperature after heating 26°–28° C. ($T_2$).
Nitrogen flow rate between 0.5 and 2mt/sec.
Time about 12 hours.
Relative humidity entry to drying region (point $I_1$) 12–14%.
Relative humidity exit of drying region (point $I_2$) 70–80%.

3rd stage:
Nitrogen temperature after cooling –15° C. ($T_1$).
Nitrogen temperature after heating 26°–28° C. ($T_2$).
Nitrogen flow rate between 0.5 and 2 mt/sec.
Time about 12 hours.
Relative humidity entry to drying region (point $I_1$) 6–7%.
Relative humidity exit of drying region (point $I_2$) 45–50%.

4th stage:
Final drying
Nitrogen temperature after cooling –40° C. ($T_1$).
Nitrogen temperature after heating 26°–28° C. ($T_2$).
Nitrogen flow rate between 0.5 and 2 mt/sec.
Time about 12 hours.

5th stage:
Product discharge, preparation of a new load. Complete removal of water from the cooling coil and purging the oven by nitrogen circulation at 70°–80° C. for two hours, cooling to 20° C. and loading new product.

The nitrogen flow rate through the drier is adjusted on the basis of the required degree of drying. Typically, at the beginning of a drying cycle, flow rates between 5 and 20 mt/sec are used, while for subsequent stages flow rates lower than 2 mt/sec. are preferred.

The assays herein below described were carried out on 9 samples coming from 9 different batches obtained according to the previous example.

Absence of degradation products

The degradation products are water-soluble low molecular weight peptides which are formed during hydrolytic degradation of collagen.

Their amount in the sheet of collagen of the invention, which is insoluble in water, are determined by evaluating the amount of water-soluble products in the aqueous phase of aqueous dispersions of the collagen sheet according to the procedure described below. Sheets of type I collagen obtained as previously described are cut into square pieces of approximately 16 cm² and suspended in deionized or distilled water in an exactly weighed amount of about 100 mg in 100 ml. The dispersion so obtained is kept under vigorous mechanical stirring at a speed of about 200 oscillations/min., at room temperature, (+20°/+25° C.), for a time of 1 hour.

The aqueous phase is separated by means of filtration with a Whatman filter (n° 42). The absorbance at 207 nm of samples preparaed by diluting 1:5 with HCl 1N the aqueous solution so obtained was measured and the amount of water-soluble products calculated by comparison with the absorbance values of standard reference solutions containing gelatin in HCl 1 N with a concentration of between 0.125% and 0.75% weight/volume. Every reference solution is diluted 1:150 with HCl 1N.

The amount of water-soluble products found is 1.5% weight/weight (medium value found for 9 different batches of sheets of collagen prepared according to the above example).

The amount found corresponds to the amount ranges present in the type I collagen used as starting material, thus indicating that during the present process no significant chemical degradation of collagen has occured.

Electron Microscopy Assay

Sections of the sheet prepared as above described were fixed in a glutaraldehyde-osmium medium.

The samples were observed on an electron microscopy, using mixtures of uranyl acetate and lead citrate were used as the contrast medium.

The test allows to investigate the morphology of the sheet of type I collagen and shows the presence of the collagen fibrils and of the basic, rigid triple-helical structure which is peculiar of the "native" collagen structure.

Enzymatic Degradation Assay 20 mg of a sheet of collagen prepared as above described are placed into a test-tube together with AcOh/glycerin (2 ml), Tris-HCl (2 ml) and 1 ml of tripsin in Tris-HCl. The samples are placed in a 25° C. environment for 2 hours.

The amount of collagen which dissolved after enzgmatic degradation is evaluated by subjecting the resulting solutions to acidic hydrolisis according to the conditions reported by Diamond A.M., Gorham S.D., Etherhington D.J., Robertson J.G., Light N.D. in Matrix, Vol.11/1991, pag. 321–329,Gustav Fisher Verlag, Stuttgart, 1991. The amount of hydroxyproline in the solution resulting from the hydrolisis is measured by means of ultraviolet spectroscopy as described herein below.

The solution obtained from the acidic hydrolisis is filtered by means of a Wathman filter n° 42. 0.3 ml are added with 0.7 ml of water, 1 ml of a 0.25% aqueous $CuSO_4$ solution, 1 ml of a 10% aqueous NaOH solution and 1 ml of a 6% aqueous $H_2O_2$ solution. After stirring for 5 min, the test-tube is placed into a water bath at 80° C., then cooled into an ice-bath and added with a $H_2SO_4$ solution obtained by diluting $H_2SO_4$ 1:11 with water, and with 2 ml of a 5% solution of p-dimethylaminobenzaldheyde in n-propylalcohol. After heating in a water bath at 70° C., the mixture is cooled to room temperature and the sample is spectrofotometrically analysed at 506 nm against a blank solution. The hydroxyproline amount is calculated with the method of the standard calibration curve. Thus, 40 mg of hydroxyproline are exactly weighed and placed into a graduated flask, then dissolved and diluted with distilled water up to a final volume of 50 ml. 4 ml of the solution so obtained are diluted with 100 ml of water. The stock solution (S.S.) obtained is then diluted as follows : 0.25 S.S.+0.75 ml of $H_2O$; 0.50 S.S.+ 0.50 ml of $H_2O$; 0.75 S.S.+0.25 ml of $H_2O$ and treated according to the method used for the sample to be tested.

(See also Foster Dee Snell, Cornelia T. Snell, "Colorimetric Methods of Analysis", Vol. 4, pag. 195, 3rd Ed., D. Van Nostrand Company, Inc., N.Y., 1954).

The medium values found after analysis of 9 batches of product ranges from 2% to 5% weight/volume.

Proteic nitrogen content

The nitrogen content is determined according to the Kjeldhal method as modified by Wieninger, using a Gerhardt apparatus comprising a mineralizer and a distiller. About 500 mg of product, exactly weighed, are placed into the flask of the distillation apparatus and added with 500 mg of selenic mixture and with 25 ml of concentrated sulfuric acid. The flask is gradually heated, first up to carbonization of the product, and then until a perfectly clear solution is obtained. The solution is diluted with distilled water, then made alkaline by adding a 40% NaOH aqueous solution. The ammonia formed is collected by steam distillation and trapped into 25 ml of 1 M $H_2SO_4$. The residual acidity is titrated with 1N NaOH, using the indicator according to Mortimer (Special Indicator 5, Merck$^R$). The total nitrogen percent of the tested sample is calculated according to the following formula:

$$(25-A)\times 0.14 \times 100/P$$

wherein

A=ml of NaOH 1N used; and

P=weight of the tested gel sample. (See also Riemschneider R. and Chik W.H. in Cosmetic and Toiletries/61, Vol. 91, May 1979).

The medium value found after analysis of 9 batches of product is $\geq 95\%$ weight/weight, calculated on the dried substance.

Hydroxyproline content

The hydroxyproline content is determined by oxidation followed by decarboxylation to pyrrol, followed by complexation with p-dimethylamino benzaldehyde and UV spectrofotometric determination in comparison with that of a reference standard solution.

Particularly, about 150 mg, exactly weighed, of collagen are placed into a Sovirel test-tube provided with a teflon packed screw plug are added with 6 ml of 1N HCl and kept for 24 hours in a bath oil thermoregulated at 121° C. The mixture obtained is cooled and filtered trough a sintered glass filter G4. 1 ml of the clear solution is transferred into a graduated flask and diluted with water up to a final volume of 200 ml. 1 ml of the solution so obtained, 1 ml of a 10%. aqueous NaOH solution and 1 ml of a 6% aqueous $H_2O_2$ solution are placed into a 10 ml test-tube. After stirring for 5 min, the test-tube is placed into a water bath at 80° C., then cooled into an ice-bath and added with a $H_2SO_4$ solution obtained by diluting $H_2SO_4$ 1:11 with water, and with 2 ml of a 5% solution of p-dimethylaminobenzaldheyde in n-propylalcohol. After heating in a water bath at 70° C., the mixture is cooled to room temperature and the sample is spectrofotometrically analysed at 506 nm. The hydroxyprolyne amount is calculated with the method of the standard calibration curve. Thus, 40 mg of hydroxyproline are exactly weighed and placed into a graduated flask, then dissolved and diluted with distilled water up to a final volume of 50 ml. 4 ml of the soluiton so obtained are diluted with 100 ml of water. The stock solution (S.S.) obtained is then diluted as follows : 0.25 S.S.+0.75 ml of $H_2O$; 0.50 S.S.+0.50 ml of $H_2O$; 0.75 S.S.+0.25 ml of $H_2O$ and treated according to the method used for the sample to be tested. (See also Foster Dee Snell, Cornelia T. Snell, "Colorimetric Methods of Analysis", Vol. 4, pag. 195, 3rd Ed., D. Van Nostrand Company, Inc., N.Y., 1954).

The medium value found after analysis of 9 batches of product is $\geq 12\%$ weight/weight.

Water content

The water content is determined by analysis according to Karl Fisher method or by the weight difference found for a sample after drying at 105° C. for 4 hours.

The water content at the end of the drying cycle is 4.5% (medium value obtained from 9 batches). The analysis is generally carried out within 2 hours after the end of the drying cycle, on samples maintained in an anhydrous environment, e.g. under a nitrogen atmosphere.

Determination of acetates, chlorides and phosphates Apparatus: DIONEX chromatograph mod. 4506-LCM2 equipped with a conductivity detector. Column: Omnipax-500 equipped with a pre-column.

Operative conditions:

Eluent:

1) 1mN NaOH 2) 200 mN NaOH 3) 5% aqueous solution of methanol

Gradient:

| | Eluent | | |
|---|---|---|---|
| Times | 1 | 2 | 3 |
| | % | | |
| 0 | 75 | 0 | 25 |
| 5 | 75 | 0 | 25 |
| 10 | 60 | 15 | 25 |
| 20 | 35 | 40 | 25 |
| 25 | 75 | 0 | 25 | flow: 1 ml/min

Detector base line: 100 µS

Injection: 25 µl

Blanker: 100 ml of 2N $H_2SO_4$ are diluted with water up to a final volume of 2000 ml.

Standard Solution:

20 mg anhydrous sodium acetate, 10 mg of sodium chloride and 10 mg of potassium dihydrogen phosphate are dissolved with water up to a 100 ml volume.

Sample Solution:

500 mg of the sheet of collagen are cut into small disks of 5 mm diameter, suspended in 100 ml of water and homogenized with a ULTRATURRAX T25 apparatus at a 20.000 r.p.m. speed for 5 sec. The resulting dispersion is filtered on paper.

water: specially grade water for chromatography with 18mΩ resistance.

Quantitative Determination:

$$\% \text{ of a given ion} = \frac{A_s W_{st} 100 F_s}{A_{st} W_s}$$

$A_s$=peak area found for the sample solution $A_{st}$=peak area found for the standard solution $W_s$=sample weight $W_{st}$=weight of a given ion in the standard solution $F_s$=conversion factor (0.719 for acetate ion; 0.606 for chloride ion 0.698 for phosphate ion).
found values

| Batch | Acetate | Chloride | Phosphate |
|---|---|---|---|
| 1 | 1.30 | 0.14 | practically absent |
| 2 | 1.14 | 0.10 | " |
| 3 | 1.35 | 0.09 | " |
| 4 | 1.18 | 0.10 | " |
| 5 | 1.38 | 0.11 | " |
| 6 | 1.11 | 0.05 | " |
| 7 | 0.96 | 0.05 | " |
| 8 | 1.00 | 0.06 | " |
| 9 | 0.86 | 0.10 | " |
| 10 | 1.40 | 0.17 | " |

Typically, according to the present method, a semitransparent film with a thickness of about 200 micron is obtained. The thickness can vary in general between 0.02 and 2 mm. This represents a non-specific item for the purposes of the therapeutic application as it determines only the product absorption time but not its specific characteristics. The degree of drying can also vary as stated.

The characteristics of the film obtained are:

maintaining of the "native" structure of collagen fibre (the classical triple spiral structure of collagen has been demonstrated by the electron microscope)

absence of degradation products such as monomers or dimers of collagen not organized into fibrils, or gelatin, an indication of potential allergenicity. Typically, the amount of degradation products present in the sheet of collagen of the invention is about 1.5%, that corresponds to the amount generally present in the commercially available collagen used as started material. Thus, in the present text, the terms "absence" of degradation products and "free" from degradation products refer to the fact that the content of collagen degradation products found in the sheet of collagen of the invention is not greater than the corresponding content of the collagen used as starting material, inasmuch as no significantly detectable degradation products has occured during the present preparation method.

high protein nitrogen content (exceeding 90%) high hydroxyproline content (exceeding 12%) low absorbent power (about 10–15 times its weight against 50 times for the lyophilized product of the known art) high resistance to enzymatic attack good product transparency excellent plasticity after immersion in physiological solution.

The product obtained in this manner is sterilized by irradiation with gamma rays and used in the treatment of burns and generally all cases of skin removal or damage.

The result is excellent both in terms of tolerance (no case of allergenicity or hypersensitivity to the medicament has been recorded, the native characteristic of the product remaining unaltered during the process) and in terms of pain attenuation. The cicatrization time is very rapid and product absorption considerably longer compared with equivalent treatment using lyophilized collagen (sponge) and consequently there is lesser need to replace it. Exudate loss is very low, and much lower than that when using lyophilized collagen.

The transparency of the product means that the progress of the injury can be viewed without the need to remove the collagen sheet (generally a painful procedure).

The product can be presented in the form of sheets of different dimensions (square, rectangular, round, elliptical or others) supported or not supported by adhesives (such as plasters and other materials compatible with the collagen gel according to the invention, such as for instance silicone polymers) or by sheets of inert substances such as nylon, polyurethane, polyethylene etc., or associated during the drying process, or subsequently, with pharmacologically active substances.

The present invention is also directed to a therapeutic method of utilizing the sheets of type I collagen in accordance with the present invention to treat patients suffering from wounds.

The present method is directed toward the treatment of any kind of of wounds, e.g. resulting from surgery or from physical injuries or from a number of pathological conditions. Examples of wounds which can be treated with the sheets of collagen according to the present invention are wounds due to physical injuries, internal or external surgical wounds, burns, cutaneous ulcers, venous insufficiency ulcers, bed-sores, diabetes ulcers, ulcers associated with radiations, with drugs, with hemoglobinopathy, with high blood calcium levels, with hyper parathyroid activity, with gangrenous pyoderma. The method according with the invention is particularly directed to the cicatrization of said wounds and burns as well as to the prevention of adhesions in the internal surgery operations. For the purpose of the invention, an effective amount of the sheets of type I collagen in accordance with the present invention is topically applied to the wound, so to completely cover the area to be treated.

With regard to the size of the wound to be treated, a single sheet cut to the same dimension as the wound or more than one sheet of proper size can be applied.

The careful cleaning and sterilization of the area to be treated is typically required before applying the sheet of collagen. Before application, the sheet of type I collagen according to the invention is preferably soaked with steril water, such as with a sterile saline solution, so to be properly softened and made more plastic and easy to be applied; generally, the wound to be treated is also wet with the same sterile solution before applying the collagen sheet.

The collagen sheets of the invention can be applied in a single layer, as in the case of cicatrization of superficial wounds which do not lose excessive amounts of essudates, or in multiple layers (two or three layers), as in the case of cicatrization of deep wounds whith a lot of essudate.

Once covered the area to be treated, the sheet collagen of the invention may be covered with gauze and fixed with anallergic plasters, or can be sutured with suitable surgical threads. The course of cicatrization is periodically evaluated by visual inspection (every 24 or 48 hours). Depending on the course of healing, a single administration of the collagen sheet of the invention can be sufficient. In some instances, further administration can be required, such as the additional administration of sheets when the previously administered sheet has been almost entirely absorbed, or the replacement of the previously applied sheet, when the wound results infected.

What is claim is:

1. A non-porous sheet of insoluble type I collagen gel of molecular structure, for use in the cicatrization of wounds and burns and as interposition material for preventing adhesions after internal surgical operations, characterized by the following chemical and physical properties:

free from native collagen degradation products;

possesses the rigid triple-helical structure of native collagen;

has an $H_2O$ content not exceeding 20% by weight;

a thickness comprised between 0.02 and 2 mm, which is uniform over the entire surface of the sheet;

free of air bubbles except for bubbles with diameters of less than 0.034 mm, under atmospheric pressure;

an hydroxyproline content exceeding 12%;

a resistance to enzymatic attack of 2% to 5% weight/weight corresponding to the amount of collagen which has dissolved after enzymatic degradation by trypsin with respect to the weight of the tested collagen sample; and is transparent.

2. A method of preparing a sheet of insoluble type I collagen gel of molecular structure as claimed in claim 1, comprising filtering a collagen gel with a pH of 2.5–3.5 and with a collagen concentration of from 0.1 to 0.5% weight/weight, at a temperature of 10°–30° C., through a filtering mesh with a passage size of less than 0.1 mm, collecting the filtered gel in a closed vessel maintained under a vacuum of 20–60 mm Hg, provided in the region below the filtering mesh with a device for preventing incorporation of gas bubbles into the filtrate comprising a series of plates vertically placed or inclined from the perpendicular, parallel between them or radially arranged, loading the filtered gel onto trays under a relative humidity of 60–80% and at a temperature of 20°–22° C., wherein drying is effected during subsequent stages by blowing onto the sheets of collagen gel to be dried in a nitrogen stream with an oxygen content lower than 2%, with a temperature of between +20° C. and 30 30° C., decreasing during said stages the relative humidity of said nitrogen stream.

3. The method as claimed in claim 2, wherein during drying stages the nitrogen flow rate is adjusted so that it has values of from between 5 to 20 mt/sec at the beginning of drying cycle and values lower than 2 mt/sec for subsequent stages.

4. The method as claimed in claim 2, wherein the drying stage is effected in a closed cycle, wherein the relative humidity content of the nitrogen stream blown onto the gel to be dried is comprised between 30% and 1%, the nitrogen stream after the contact with the sheets of collagen gel has a relative humidity between 30% and 95% and is cooled between −40° C. to 0° C. so as to reduce its relative humidity by condensing water.

5. The method as claimed in claim 2, wherein the drying level corresponds to a $H_2O$ content of the product of 2–3%.

6. The method as claimed in claim 2, wherein the collagen gel to be filtered is obtained by dispersing fibrous collagen in an acetic acid solution with a pH of 2.5 under agitation, at temperatures ranging from 0° and +30° C., at a stirring speed of between 5 and 50 r.p.m., and diluting with an acetic acid. solution of pH 2.5–3.5 until a fluid mass is obtained.

7. The method as claimed in claim 2, wherein filtering is effected at a temperature of from 25° C. to 28° C., under a vacuum of 30 mm Hg and drying is effected under a nitrogen stream with a temperature of from +26° C. to +28° C.

8. The method as claimed in claim 2, wherein the amount of filtered gel loaded onto trays varies from 0.4 to 4 g/cm² and the gel level is between 4 to 40 mm.

9. The method as claimed in claim 8, wherein the collagen gel to be dried has a concentration of 0.5%, the loaded gel level is 10 mm, the temperature of the nitrogen stream blown onto the sheets to be dried is 26° C. to 28° C., nitrogen flow rate is between 0.5 and 2 mt/sec.; in the first drying stage nitrogen is purged until the oxygen content is less than 1%; in the second drying stage nitrogen temperature after cooling is −5° C., nitrogen temperature after heating is 26° C. to 28° C., relative humidity of the entry drying region is 12–14%; nitrogen relative humidity at the exit drying region is 70–80%; in the third drying stage nitrogen temperature after cooling is −15° C., nitrogen temperature after heating is 26° C. to 28° C., nitrogen relative humidity at the entry drying region is 6–7%, nitrogen relative humidity at the exit drying region is 45–50%; in the final drying stage nitrogen temperature after cooling is −40°, nitrogen temperature after heating is 26° C. to 28° C.

10. A non-porous transparent sheet of insoluble type I collagen gel of molecular structure, for use in the cicatrization of wounds and burns and as interposition material for preventing adhesions after internal surgical operations, obtained by filtering a collagen gel with a pH of 2.5–3.5 and with a collagen concentration of from 0.1 to 0.5% weight/weight, at a temperature of 10°–30° C., through a filtering mesh with a passage size of less than 0.1 mm, collecting the filtered gel in a closed vessel maintained under a vacuum of 20–60 mm Hg, provided in the region below the filtering mesh with a device for preventing incorporation of gas bubbles into the filtrate comprising a series of plates vertically placed or inclined from the perpendicular, parallel between them or radially arranged, loading the filtered gel onto trays under a relative humidity of 60–80% and at a temperature of 20°–22° C., wherein drying is effected during subsequent stages by blowing onto the sheets of collagen gel to be dried in a nitrogen stream with an oxygen content lower than 2%, with a temperature of between +20° C. and +30° C., decreasing during said stages the relative humidity of said nitrogen stream.

11. A non-porous sheet as claimed in claim 10, wherein the drying level corresponds to a $H_2O$ content of the product of 2–3%.

12. A porous sheet as claimed in claim 10, wherein the collagen gel to be filtered is obtained by dispersing fibrous collagen in an acetic acid solution with a pH of 2.5 under agitation, at temperatures ranging from 0° and +30° C., at a stirring speed of between 5 and 50 r.p.m., and diluting with an acetic acid solution of pH 2.5–3.5 until a fluid mass is obtained.

13. A non-porous sheet as claimed in claim 10, wherein filtering is effected at a temperature of from 25° C. to 28° C., under a vacuum of 30 mm Hg and drying is effected under a nitrogen stream with a temperature of from +26° to +28° C.

14. A non-porous sheet of insoluble type I collagen gel of molecular structure, for use in the cicatrization of wounds and burns and as interposition material for preventing adhesions after internal surgical operations, characterized by the following chemical and physical properties:

free from native collagen degradation products;

possesses the rigid triple-helical structure of native collagen;

has an $H_2O$ content not exceeding 20% by weight;

a thickness comprised between 0.02 and 2 mm, which is uniform over the entire surface of the sheet;

free of air bubbles except for bubbles with diameters of less than 0.034 mm, under atmospheric pressure; and an hydroxyproline content exceeding 12% and is transparent.

\* \* \* \* \*